United States Patent
Brekke et al.

[19]

[11] Patent Number: 6,005,161

[45] Date of Patent: *Dec. 21, 1999

[54] METHOD AND DEVICE FOR RECONSTRUCTION OF ARTICULAR CARTILAGE

[75] Inventors: John H. Brekke, Duluth, Minn.; Richard D. Coutts, San Diego, Calif.

[73] Assignee: THM Biomedical, Inc., Duluth, Minn.

[ * ] Notice: This patent is subject to a terminal disclaimer.

[21] Appl. No.: 08/481,821

[22] Filed: Jun. 7, 1995

Related U.S. Application Data

[62] Division of application No. 08/370,161, Jan. 9, 1995, which is a continuation of application No. 07/963,809, Oct. 20, 1992, abandoned, which is a continuation-in-part of application No. 07/909,605, Jul. 7, 1992, Pat. No. 5,366,508, which is a division of application No. 07/541,627, Jun. 21, 1990, Pat. No. 5,133,755, which is a continuation of application No. 07/167,370, Mar. 14, 1988, abandoned, which is a continuation of application No. 06/823,445, Jan. 28, 1986, abandoned.

[51] Int. Cl.$^6$ ........................................................ A61F 2/28
[52] U.S. Cl. .................................................................. 623/16
[58] Field of Search ................................... 623/1, 11, 12, 623/16, 18, 66; 424/422, 423, 424

[56] References Cited

U.S. PATENT DOCUMENTS

| | | | |
|---|---|---|---|
| 4,846,835 | 7/1989 | Grande | 623/11 |
| 5,041,138 | 8/1991 | Vacanti et al. | 623/16 |
| 5,133,755 | 7/1992 | Brekke | 623/16 |
| 5,366,508 | 11/1994 | Brekke | 623/16 |

*Primary Examiner*—David Isabella
*Attorney, Agent, or Firm*—Alan D. Kamrath; Peterson, Wicks, Nemer & Kamrath, PA

[57] ABSTRACT

A biodegradable device for facilitating healing of structural voids in bone, cartilage as well as soft tissue is disclosed in the most preferred form including a porous macrostructure made from a biodegradable polymer and a chemotactic ground substance in the form of an RGD attachment moiety of fibronectin formed as a porous microstructure. For repair of articular cartilage, harvested precursor cells are secured to the biodegradable carrier which is shaped for press fitting into the articular cartilage lesion. In the most preferred form, the chemotactic ground substance enhances the attractiveness of the biodegradable device for cellular attachment at the site of repair and also facilitates the attachment of free, precursor cells such as chondrocytes and bone marrow to the biodegradable device. In the most preferred form, biological modifiers such as transforming growth factor B and basic fibroblastic growth factor is incorporated in the biodegradable device to mediate cellular activity and regulate cellular functions.

6 Claims, 3 Drawing Sheets

METHOD AND DEVICE FOR RECONSTRUCTION OF ARTICULAR CARTILAGE

CROSS REFERENCE

The present application is a division of application Ser. No. 08/370,161 filed Jan. 9, 1995, pending, which in turn is a continuation of application Ser. No. 07/963,809 filed on Oct. 20, 1992, which is now abandoned and in turn is a continuation-in-part of application Ser. No. 07/909,605 filed Jul. 7, 1992, now U.S. Pat. No. 5,366,508, which in turn is a divisional application of application Ser. No. 07/541,627 filed Jun. 21, 1990, now U.S. Pat. No. 5,133,755, which in turn is a continuation application of application Ser. No. 07/167,370 filed Mar. 14, 1988, which is now abandoned and in turn is a continuation application of application Ser. No. 06/823,445 filed Jan. 28, 1986, which is now abandoned.

BACKGROUND

The present invention relates generally to techniques and devices for repair of cartilage defects, and specifically to techniques and devices for repair of articular cartilage defects, and particularly to techniques and devices for repair of articular cartilage defects utilizing cell grafts secured in the articular cartilage deficiency utilizing a carrier formed from biodegradable material such as polylactic acid.

The successful repair of articular cartilage defects has eluded clinical medicine and has motivated the investigation of the use of organic and inorganic materials such as collagen matrices (see U.S. Pat. No. 4,846,835), carbon fibers, polyvinyl alcohol sponges, and acrylateamide sponges for the repair of osteochondral defects. The biological acceptability rates resulting from the use of these materials have remained low; however, some promising results have emerged and have encouraged further investigation into the use of synthetic materials for the repair of osteochondral defects.

Polylactic acid, a high-molecular-weight polymer of the cyclic diester of lactic acid, has been utilized as suture material, as surgical dressing following dental extraction, and as surgical rods, plates, and screws. Polylactic acid has several advantages as a biodegradable prosthetic material. It is a nontoxic workable material which can be manufactured into a spectrum of forms with different physical characteristics; it elicits minimal immunological or inflammatory response and has good tissue compatibility; it allows the gradual ingrowth of fibrous connective tissue; and it undergoes hydrolytic deesterification to lactic acid, a normal metabolite of carbohydrate metabolism. The use of polylactic acid by itself has been investigated for the repair of articular defects in rabbits such as reported in *Reconstruction of Rabbit Knee Articular Defects with a Polylactic Acid Matrix*, R. D. Coutts et al., Orthopedic Research Society, Feb. 5–8, 1990.

It has also been found that the repair of articular cartilage lesions can be enhanced by the transplant of cells having the ability to differentiate into cartilage cells, i.e. marrow, periosteal or perichondrial cells and that will proliferate and produce a matrix that will replace hyaline articular cartilage. Specifically, periosteal grafts have been sutured to the end of a polylactic plug such as reported in *The Use of Polylactic Acid Matrix and Periosteal Grafts for the Reconstruction of Rabbit Knee Articular Defects*, H. P. von Schroeder et al., Journal of Biomedical Materials Research, Volume 25, 329–339 (1991). The source of cells is carried by and locked into place in the lesion by the polylactic plug which serves as a template for bone formation if it is in contact with bone tissue. The biodegradable device utilized in the investigations reported above was formed of polylactic acid and was of the type shown and described in U.S. Pat. No. 4,186,448 (which is hereby incorporated herein by reference).

The cells carried by the biodegradable device are the mediators of repair tissue and must become attached at the site of repair in order to effect that repair. Thus, a need exists for enhancing the attractiveness of the biodegradable device for cellular attachment at the site of repair. Further, a need exists for facilitating the attachment to the biodegradable device of free cells which act as the source of precursor cells for the production of connective tissue.

SUMMARY OF THE INVENTION

The gross structure of the body member of the device is composed of a biologically acceptable, biodegradable polymer arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448). Polylactic acid (PLA) is the polymer currently used to form the gross structure. Other members of the hydroxy acid group of compounds can also be used. The gross, or macro, structure of the invention fulfills three major functions for osteogenesis: 1) restoration of mechanical architectural and structural competence, 2) provides biologically acceptable and mechanically stable surface structure suitable for genesis, growth and development of new non-calcified and calcified tissue, 3) functions as a carrier for other constituents of the invention which do not have mechanical and structural competence.

The microstructure of the body member is composed of a chemotactic ground substance which in a preferred form is hyaluronic acid (HA). Interstices of the gross (polylactic acid) structure of the body member are invested with the chemotactic ground substance in the form of a velour having the same architecture of interconnecting voids as described for the gross structure, but on a microscopic scale. Functions of the chemotactic ground substance microstructure are listed as:

1) attraction of fluid blood throughout the device, 2) chemotaxis for mesenchymal cell migration and aggregation, 3) carrier for osteoinductive and chondroinductive agent(s), 4) generation and maintenance of an electro-negative wound environment, 5) agglutination of other connective tissue substances with each other and with itself. Other examples of chemotactic ground substance are fibronectin and, especially for the reconstruction of articular cartilage, an RGD attachment moiety of fibronectin.

The osteoinductive agent, bone morphogenetic protein, has the capacity to induce primitive mesenchymal cells to differentiate into bone forming cells. Another osteogenic agent, bone derived growth factor, stimulates activity of more mature mesenchymal cells to form new bone tissue. Other biologically active agents which can be utilized, especially for the reconstruction of articular cartilage, include transforming growth factor B and basic fibroblastic growth factor.

In a further aspect of the present invention, the biodegradable graft substitute device acts as a carrier for precursor cells harvested for the production of connective tissue and secured to the device, with the device and precursor cells secured thereto being press fit into the site of repair. In a preferred aspect of the present invention, the chemotactic ground substance (in the form of an RGD attachment moiety of fibronectin) facilitates the attachment of free, precursor cells carried to the repair site.

Significant advantages and features of the present invention include:

1. Eliminate the need to remove autologous bone from the iliac crest or rib for grafting purposes;
2. Functions as part of the internal fixation apparatus to secure itself in the bone void being grafted;
3. Functions as a carrier for biologically active agents (i.e. chemotactic substances);
4. Functions as a carrier for osteoinductive/osteogenic and/or chondroinductive/chondrogenic agents, as well as other therapeutic substances (i.e. antibiotics);
5. Creates an electronegative environment which is conducive to osteogenesis in its own right;
6. Completely biodegradable; eliminates need for second surgeries to remove device;
7. Creates a carrier for precursor repair cells for repair sites; and
8. Facilitates the attachment of free, precursor cells to the device and to the repair site.

Objects of the present invention include:

1. Provide a biodegradable structure to carry and support a chemotactic ground substance which is in the form of a filamentous velour (having incomplete, interconnecting intersticies);
2. Generates electronegative potentials by maintaining an HA-fluid phase and PLA structural phase interface, as well as by the electronegative chemical property of HA alone;
3. Creates biophysical conditions and environment such that exogenous electric signals can be applied to the device (Osmed biodegradable bone graft substitute) to produce a synergistic effect with the endogenous currents generated by HA/PLA surface interactions and the intrinsic electronegativity of HA substance;
4. Granular form—each granule loaded with chemotactic ground substance (hyaluronic acid, fibronectin, an RGD attachment moiety of fibronectin) and biologically active agent (bone morphogenetic protein, bone derived growth factor, transforming growth factor B and/or basic fibroblastic growth factor);
5. Unique juxtaposition of polylactate, hyaluronic acid and chemical osteoinductive/osteogenic and/or chondroinductive/chondrogenic agents;
6. Unique arrangement of constituents potentiates osteoinductive effects of exogenous electric potentials and electromagnetic fields;
7. Juxtaposition of a chemotactic ground substance with a biodegradable polymer of either solid, open cell meshwork form, or in either form or both forms;
8. Provides a biodegradable structure to carry and support precursor repair cells for repair sites; and
9. Creates conditions and environment for facilitating the attachment of free, precursor cells for carriage to the repair site.

DESCRIPTION OF THE PREFERRED EMBODIMENTS

Figure 1:
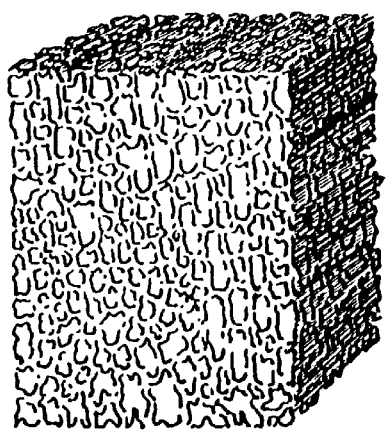
FIG. 1 illustrates a sectional view of the gross structure and architecture of the present invention including randomly shaped, randomly positioned, and randomly sized interconnecting voids.

A device and method are provided for treating mammalian bone deficiencies, defects, voids and conformational discontinuities produced by congenital deformities, osseous and/or soft tissue pathology, traumatic injuries (accidental and/or surgical) and functional atrophy.

The present invention provides a one piece molded body member composed of four substances, each of which contributes to the invention a specific requirement or requirements for osteoneogenesis. Taken as a whole, the functions of these device constituents are integrated into a single body member which, when implanted into a bone defect, has the capacity to restore architectural and structural integrity, initiate osteoinduction, stimulate osteogenesis, and maintain the biological process of bone formation and remodeling while the host organism is simultaneously biodegrading the body member. The ultimate result of the functioning of this invention is formation of healthy, viable bone tissue where there was not bone before, while, simultaneously, the entire device is hydrolyzed and completely metabolized by the host organism.

The body member is composed of four disparate elements. Each of these entities contributes to the invention essential biologic function or functions prerequisite to the processes of osteoneogenesis. There are five such functions listed as follows:

1. Structural Competence—gross structure of the invention restores mechanical, architectural and structural competence to the bone defect while it simultaneously provides mechanical support and structural surface areas for the dynamic biological processes of wound healing and osteogenesis;
2. Chemotaxis—attraction of (mesenchymal) cells of varying degrees of maturation into the wound void from adjacent healthy tissues and from the collateral circulation servicing the wound void;
3. Electronegative Field—production and maintenance of an electronegative environment within the healing bone wound by electrokinetic and electrochemical means;
4. Osteoinduction—production by chemical agents of fundamental genetic changes in primitive mesenchymal cells (perivascular pericytes) such that their future course of maturation is predetermined to result in their transformation into mature bone forming cells (osteoblasts).
5. Osteogenesis—stimulation of biosynthetic processes of cells already induced to mature as osteoblasts.

Each of the body member constituents and their osteogenic functions are described in the following sections; first in general terms, then in specific detail.

Elements and Biological Functions of Body Member Constituents

Biodegradable Polymeric Macrostructure

The gross structure of the body member is composed of a biologically acceptable, biodegradable polymer arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448).

The material currently used to form the gross structure is the polymer of lactic acid (polylactic acid). This is a specific example of a biodegradable polymer. Lactic acid is a member of the hydroxy acid group of organic compounds. Other members of this group, such as glycolic acid, malic acid and alpha hydroxybutyric acid, can also be polymerized into biodegradable polymer suitable for use in the gross structure of this invention. In addition, compounds of other metabolic pathways, such as fumaric acid, can be polymerized and used in similar manner.

The gross structure is composed of a poly(hydroxy) acid and in the form of an interconnecting, open-cell meshwork, duplicates the architecture of human cancellous bone from the illiac crest and possesses physical property (strength) values in excess of those demonstrated by human (mammalian) illiac crest cancellous bone. The gross structure of the invention maintains physical property values at least equal to those of human, illiac crest, cancellous bone for a minimum of 90 days following implantation.

Biodegradable Macrostructure

The gross, or macro, structure of the invention fulfills three major functions required for osteogenesis. These functions are:

1. restoration of mechanical, architectural and structural competence to the bone void being treated;
2. providing a biologically acceptable and mechanically stable surface structure suitable for genesis, growth and development of new non-calcified and calcified connective tissue;
3. acting as a carrier for the other constituents of the invention which do not have mechanical and structural competence.

Biodegradation of the hydroxy acids is initiated by the process of hydrolysis. The polymer, at body temperature, takes on water and is first hydrolyzed to the dimer of lactic acid, lactide. Lactide units are further hydrolyzed to free lactic acid which is then incorporated into adjacent cells and metabolized, via the Kreb's Cycle, to energy (in the form of adenosine triphosphate), water and carbon dioxide.

Biodegradable Polymeric Microstructure

The microstructure of the body member is composed of a chemotactic ground substance. Glycoproteins such as collagen and fibronectin would be suitable chemotactic ground substances for this invention. The glycosamino-glycan, hyaluronic acid, is another suitable chemotactic ground substance for this device. Hyaluronic acid is the chemotactic ground substance of choice because it is commercially available in quantity and because it possesses several favorable properties in addition to its chemotactic qualities.

Hyaluronic acid is a prime constituent of all naturally occurring, mammalian connective tissues (calcified as well as non-calcified connective tissues). The hyaluronic acid used can be synthesized by bacteria such as that used in known processes. Following purification of the material, the hyaluronic acid can be processed into a velour composed of hyaluronate fibrils with intercalated voids of microscopic dimensions. Each void communicates with all others within the hyaluronic velour.

Interstices of the gross (polylactic acid) structure of the body member are invested with chemotactic ground substance, such as the velour of hyaluronic acid. In final form, the velour of chemotactic ground substance completely occludes all of the interstices of the polylactic acid macrostructure of the body member.

The velour of chemotactic ground substance (hyaluronic acid) accomplishes several biochemical and biomechanical functions essential for bone wound healing and osteogenesis. These functions, five in number, are listed as follows:

1. Attraction of Fluid Blood—Hyaluronic acid is extremely hydrophilic. It is capable of taking on between 500× and 1,000× its own weight in water. It does, therefore, attract any water based fluid, such as whole blood, blood plasma and serum. This quality of hyaluronate is valuable for drawing fluid blood to all regions of the bone void being treated and establishing a viable blood clot in all areas of the bone void in question.
2. Chemotactic for Mesenchymal Cell Migration and Aggregation—By virtue of its hydrophilia and by virtue of specific cell binding cites, hyaluronic acid is an important matrix (or substrate) for embryonic and wound healing mesenchymal cell migrations, proliferations and aggregations. Its presence facilitates movement of undifferentiated mesenchymal cells from their points of origin in surrounding healthy tissues and collateral circulation to all regions of the bone void under treatment.
3. Carrier for Osteoinductive/Osteogenic Agent(s)—By chemical binding, as well as by mechanical entrapment, hyaluronic acid is capable of being joined to osteoinductive/osteogenic agents such as the bone morphogenetic protein (BMP) and the bone-derived growth factor (BDGF).
4. Generation and Maintenance of an Electronegative Environment—The chemical, hyaluronic acid, is strongly electronegative. Its presence in a fresh wound will, by chemical means, cause the wound environment to be electronegative. When saturated with fluid blood (80% water), the hyaluronate velour becomes a highly viscous gel or plasma with an electronegative charge. An electrokinetic event is generated at the interface of the hyaluronate plasma and the polylactate of the macrostructure whenever there is a slight structural distortion of the body member. The electrokinetic event is a second source of electronegativity related to, but independent from, the electronegative chemical properties of hyaluronic acid.
5. Agglutinate Other Connective Tissue Substances with Each Other and with Itself—Hyaluronic acid is the core protein of glycosaminoglycan and proteoglycan aggregates. It also binds, by virtue of specific receptor sites, to the glycoproteins (specifically collagen, fibronectin and osteonectin) and to the pericellular matricies of undifferentiated mesenchymal cells and mature connective tissue cells.

This wide variety of connections to cells, as well as to the prime constituents of the intercellular matrix, makes hyaluronic acid one of the central players (participants) in the growth, development and maintenance of mature connective tissue of both non-calcified and calcified varieties.

Hyaluronic acid is hydrolyzed by the enzyme, hyaluronidase. This enzyme is produced in the lysosomes of the cells which develop with the hyaluronate polymer matrix.

Osteoinductive/Osteogenic Substance(s)

Located within the organic phase of bone tissue are substances which have the capacity to induce primitive mesenchymal cells to differentiate into bone forming cells (osteoblasts) or stimulate activity of more mature mesenchymal cells. These substances are present in all normal, viable bone tissues as well as in autologous, allogeneic and xenogeneic bone graft specimen.

At least two such substances have been identified, isolated, purified, and partially characterized. One of these is the bone-derived growth factor (BDGF); the other is the bone morphogenetic protein (BMP). Predifferentiated cartilage or osteoprogenetor cells are the target cells for BDGF. BDGF is a paracrine-autocrine substance that increases activity of already active desoxyribonucleic acid (DNA) sequences to accelerated activities and rates of replication, presumably by releasing controls or constraints that would normally hold these genes in check. Bone morphogenetic protein (BMP) has, as its target cell, mesenchymal cells which are very primitive, having little or no degree of differentiation. These are known as perivascular parasites. BMP initiates activity of entirely new DNA sequences within these cells which lead to genesis of an entire embryonic type bone synthesis program.

Either or both of these substances is incorporated into the hyaluronic acid microstructure immediately prior to implantation of the device into bone void being treated. By this means these agents are evenly distributed throughout the volume of the body member and are, therefore, evenly distributed throughout the bone void being treated.

Where ever a perivascular pericyte, migrating on the hyaluronic acid microstructure, comes in contact with bone morphogenetic protein (bound to the hyaluronic acid microstructure) a new locus of osteogenesis will be formed. Likewise, osteogenesis will be accelerated where ever a more differentiated cartilage or osteoprogenetor cell contacts bone-derived growth factor in the hyaluronic acid microstructure.

FIG. 1 is a sectional view of the gross structure and architecture of the present invention consisting of randomly shaped, randomly positioned, randomly sized interconnecting voids. The incomplete partitions of these voids are composed of biodegradable structural polymer. In the case of this device, that structural polymer is polylactic acid. In this figure, as well as in FIG. 2, the randomly sized, shaped and positioned voids are empty.

Figure 2:
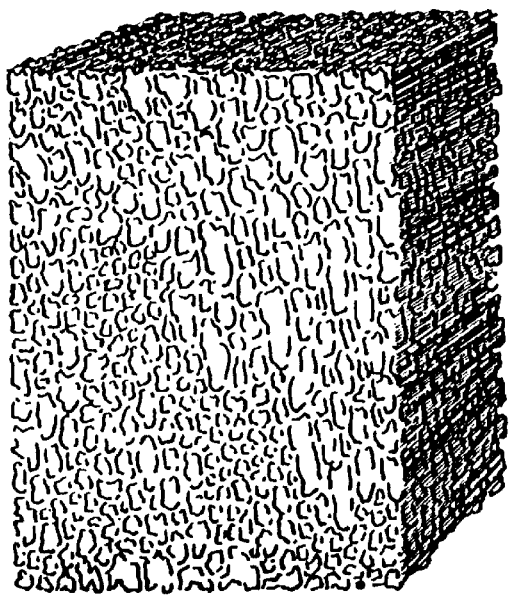
FIG. 2 is an enlarged view of FIG. 1.

FIG. 2 is an enlarged view of FIG. 1 to demonstrate more clearly the interconnecting void architecture of the structural polymer.

Figure 3:
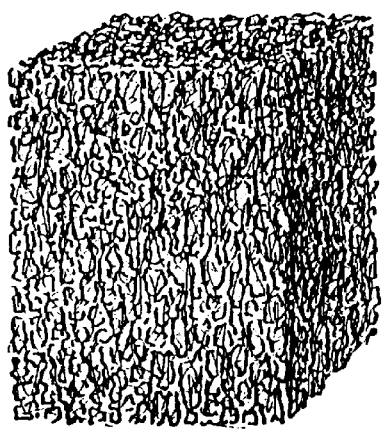
FIG. 3 is a sectional view of the gross polymeric structure after the voids of the gross structure have been invested with velour of chemotactic ground substance.

FIG. 3 is a sectional view of the gross polymeric structure shown in FIG. 1 after the voids of the gross structure have been invested with a velour of chemotactic ground substance, such as a glycosaminoglycan or glycoprotein—specifically hyaluronic acid or fibronectin. The dark heavy lines represent the structural biodegradable polymer, polylactic acid, while the fine line network represents the velour of chemotactic ground substance, i.e. hyaluronic acid.

Figure 4:
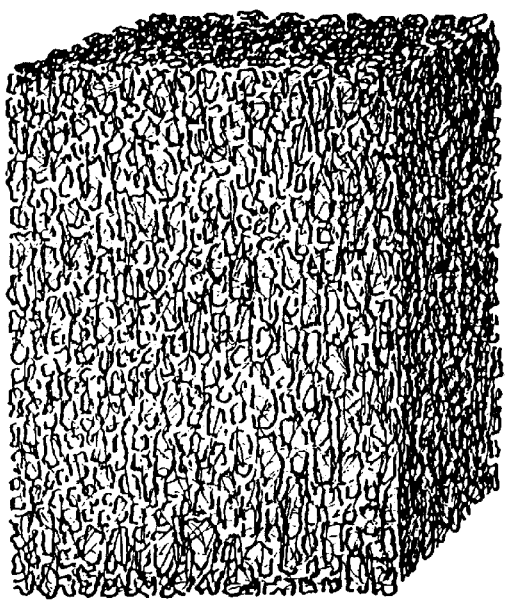
FIG. 4 is an enlarged view of FIG. 3.

FIG. 4 is an enlarged view of FIG. 3 to demonstrate more clearly the relationship between the gross polymeric structure of the device composed of polylactic acid and the micro-structure of the device composed of a filamentous network of chemotactic ground substance. The velour of chemotactic ground substance coats all surfaces of the gross structural polymer with a dense network of glycosaminoglycan or glycoprotein fibrils. This same velour of chemotactic ground substance fills or occludes all void areas between structural polymer partitions with a network of glycosaminoglycan or glycoprotein fibrils. The fibrillar network of chemotactic ground substance velour coating the surfaces of structural polymer is identical with and continuous with the fibrillar network of chemotactic ground substance velour which occludes the voids partioned by the structural polymer.

Figure 5:
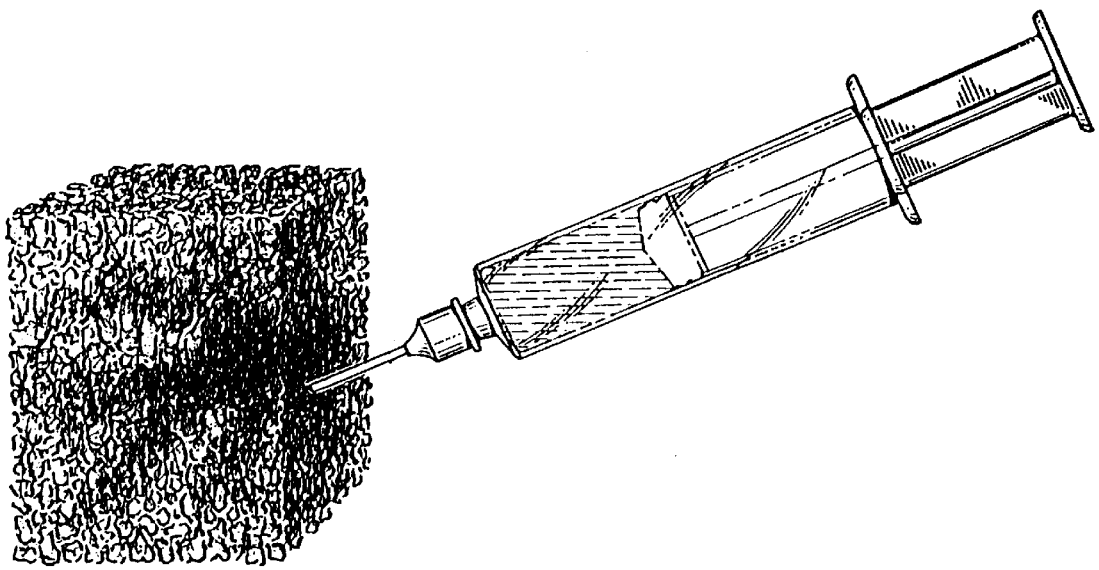
FIG. 5 is a sectional view of the FIGS. 3 and 4.

FIG. 5 is a sectional view of the device as shown in FIGS. 3 and 4. In this instance the device is being infused with a solution of biologically active agent or agents i.e. the osteoinductive agent known as bone morphogenetic protein. This solution is dispersed throughout the volume of the device, enveloping all of the fibrils of the chemotactic ground substance velour and coating all surfaces of the structural polymer.

Figure 6:
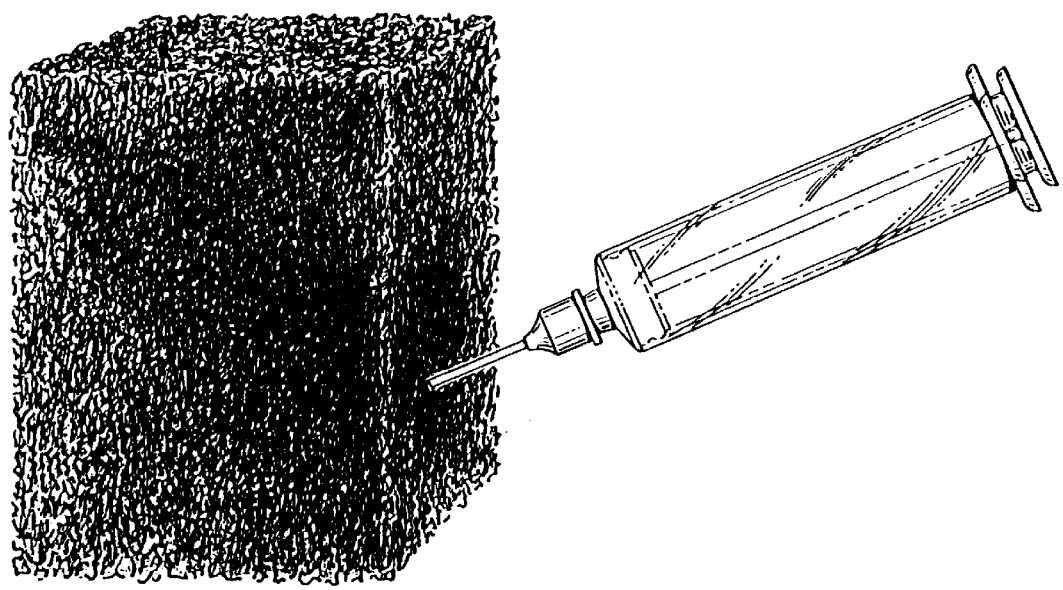
FIG. 6 is an enlarged view of FIG. 5.

FIG. 6 is an enlarged view of FIG. 5 to demonstrate more clearly the infusion of biologically active agent solution into the device and the dispersion of this solution throughout the entire volume of the body member.

The device facilitates the healing of structural voids in bone and includes a gross structure made from a biodegradable element, providing architecture and structural/mechanical integrity to the bone void being treated; a micro-structure formed from a chemotactic ground substance and integrated throughout spaces in the gross structural component; and a biologically active agent (or agents) and/or therapeutic agent (or agents) carried by either the gross or micro-structural elements or at the interface between the gross and micro-structural components.

The device also facilitates the healing of structural voids in bone and includes a gross structure formed from a biodegradable polymer which is either a homogenous poly (hydroxy) acid or a co-polymer of two or more poly (hydroxy) acids; a micro-structure formed from a chemotactic ground substance, specifically, a glycosaminoglycan(s) and/or a glycoprotein(s) or a combination of these substances; and biologically and/or therapeutically active agent (s), specifically, an osteoinductive substance known as the bone morphogenetic protein and an osteogenic substance known as the bone-derived growth factor.

The device facilitates the healing of structural bone defects whose gross structure, composed of a biodegradable polymer such as polylactic acid, is in the form of partially "enclosed, interconnected, randomly positioned and randomly sized and shaped voids; each void connecting with the others and communicating with the exterior of the body" (quoted portion from U.S. Pat. No. 4,186,448). The device also facilitates the healing of structural bone defects whose micro-structure, composed of a biodegradable chemotactic ground substance such as the glycosaminoglyca known as hyaluronic acid or the glycoprotein known as fibronectin, is likewise in the form of partially complete, interconnecting, randomly positioned and randomly sized and shaped intersticies; each interstice connecting with all the others and communicating with any exterior location of the chemotactic ground substance.

The device also facilitates the healing of structural bone defects in which the filamentous velour of chemotactic ground substance is invested into the inter-connecting voids (intersticies) of the polymeric gross structure.

Juxtaposition of different forms of the constituent elements occurs as solid form of structural polymer with open-cell meshwork (velour) form of the chemotactic ground substance; solid form of chemotactic ground substance with open-cell meshwork (velour) form of structural polymer; and solid form of chemotactic ground substance with solid form of structural polymer.

Therapeutic and/or biologically active agent(s) can be carried by the structural polymer. Therapeutic and/or biologically active agent(s) can be carried by the chemotactic ground substance. Therapeutic and/or biologically active agent(s) can be carried by entrapment between the chemotactic ground substance and the structural polymer at their interface.

MODE OF OPERATION

The net result of these biological activities is establishment of multiple foci of osteogenesis within the implanted body member. As these individual foci of osteogenesis enlarge they coalesce into larger volumes of new bone tissue. Simultaneously, cells involved in the osteogenic process are metabolizing free lactic acid that is constantly generated by hydrolysis of the polylactic acid macrostructure. These same cells are also producing the enzyme, hyaluronidase, which hydrolyzes hyaluronic acid. The osteoinductive/osteogenic agents are metabolized by the cells to which they become attached.

Ultimately the polylactate macrostructure and the hyaluronate microstructure are hydrolyzed and metabolized by the variety of mesenchymal cells which compose the genealogy of the osteoblasts, by various scavenger cells such as macrophages and by occasional foreign body giant cells. The bone void volume formerly occupied by constituents of the body member becomes progressively occupied by new bone generated from the multiple foci of osteoneogenesis initiated in the hyaluronic acid microstructure by osteoinductive/osteogenic agents.

The device is applied in the same manner as any autologous or allogeneic bone graft material. Just before insertion into the bone void being grafted, the macro and microstructure complex is injected with a solution of sterile water, plasma or serum containing the osteoinductive and/or osteogenic agent (bone morphogenetic protein and/or bone derived growth factor) rather than simply moistening it with sterile saline, whole blood or blood plasma as is current practice.

Various flanges, rods, bars and other appendages are used to affix the macrostructure of the device to surrounding healthy bone using wires, screws (also of polylactic acid) and PLA staples and sutures.

The macro-structure is formed by a vacuum foaming process using an adaptation of standard lyophilization techniques.

The micro-structure is formed by lyophilization of the alcohol gel solution of hyaluronic acid after the interstices of the macrostructure have been invested with the HA gel.

The osteoinductive/osteogenic agent is injected into the PLA/HA complex structure immediately before the device is inserted into the bone void being treated. This is done by the operating surgeon or a surgical assistant.

The open-cell meshwork architecture of hyaluronic acid polymer is composed of hyaluronate in the form of a filamentous velour. This velour is characterized by randomly positioned, randomly shaped and randomly sized voids all of which are incompletely partitioned. These incomplete voids are, in fact, intercommunicating interstices each of which communicates with all of its neighboring voids and possesses and unimpeded avenue of communication with any point on the surface of the hyaluronic acid portion of the device.

Utilizing the hydrophilic properties of hyaluronic acid, a sterile solution of biologically active agent (in this case the bone morphogenetic protein and/or bone derived growth factor) is evenly distributed throughout the volume of the device and the agent itself is attached to the hyaluronic acid velour such that cells invading the device are attracted to the substance and held in contact with it by virtue of hyaluronate's chemotactic properties.

Hyaluronic acid is strongly electronegative. Electronegative wound environments have been demonstrated to be favorable for osteogenesis. By virtue of its electronegative properties and its uniform, wide spread distribution throughout the volume of the device (and, therefore, the volume of the wound), hyaluronate, in the form of an open-cell velour, creates an electronegative wound field until it is biodegraded past a critical minimum concentration.

Examples of chemotactic ground substances are: hyaluronic acid and fibronectin. Examples of biodegradable structural polymers are: the poly(hydroxy) acids (i.e. polylactic acid, polyglycolic acid) and polysulfone.

In the repair of articular cartilage lesions according to the preferred teachings of the present invention, the chemotactic ground substance which in the preferred form is an RGD attachment moiety of fibronectin, the biologically active portion of proteins that function to attach cells, can be carried by the porous macrostructure and specifically can be located in the voids and carried by and separate from the biodegradable polymer preformed into the gross structure, with the voids interconnecting and communicating with all the others and substantially the entire exterior of the gross structure, with the biodegradable polymer being preformed into the gross structure prior to the introduction of the chemotactic ground substance. Additionally, biological modifiers can be incorporated into the biodegradable device, with the biological modifiers being in the form of growth factors in the most preferred form. Growth factors are the mediators of cellular activity and either up-regulate or down-regulate certain cellular functions, with growth factors being utilized to stimulate cell division or to stimulate the cell to produce the extracellular matrix. To enhance cell replication and matrix production in the repair of articular cartilage lesions, biological modifiers such as transforming growth factor B or basic fibroblastic growth factor can be utilized to stimulate the appropriate cellular response that in turn would produce the repair.

Figure 7:
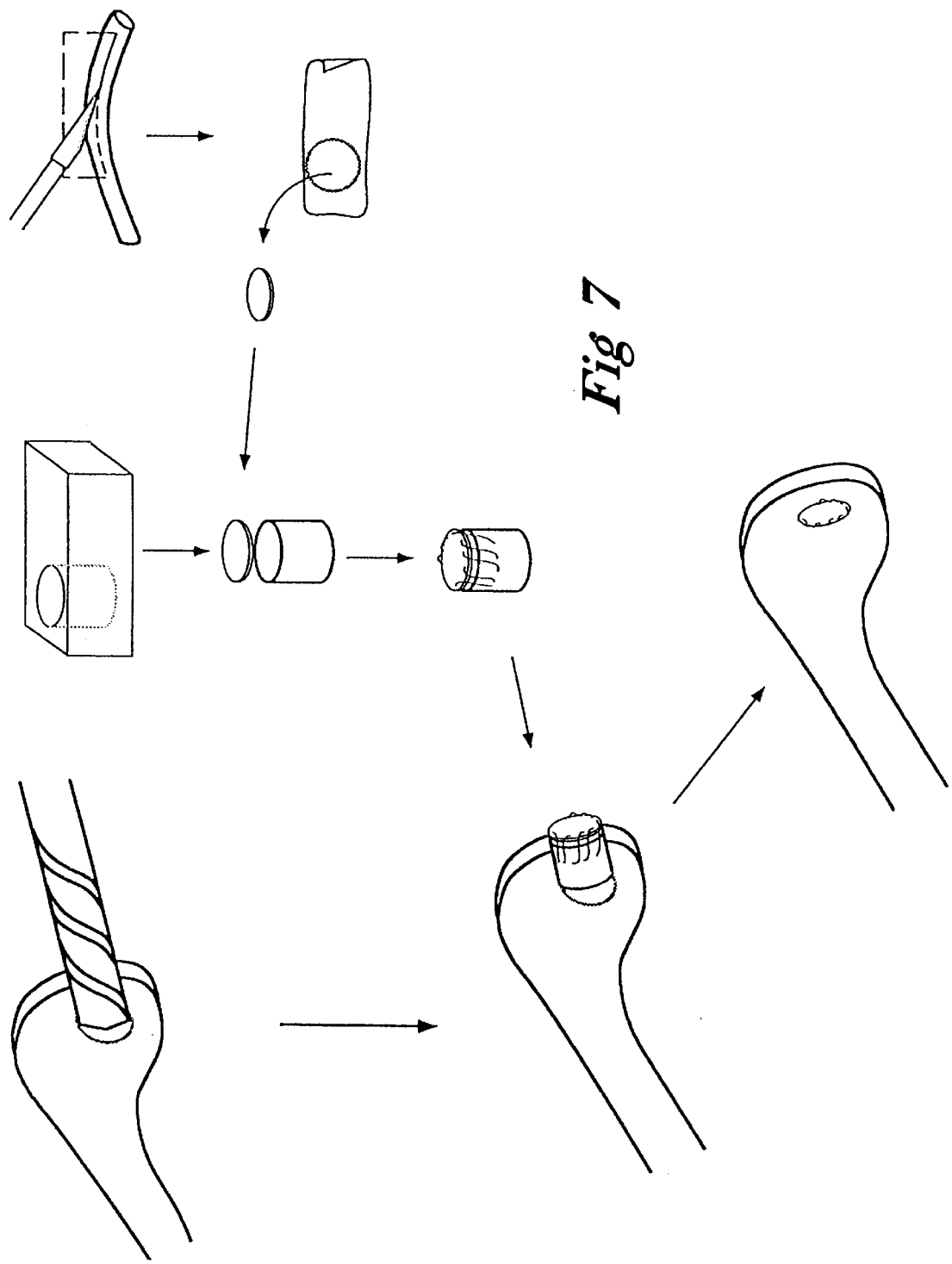
FIG. 7 is a diagramatic view of a method for reconstruction of articular cartilage according to the preferred teachings of the present invention.

In the repair of articular cartilage, the biodegradable graft substitute device acts as a carrier for cells which have demonstrated the ability to differentiate into cartilage cells, i.e. bone marrow, periosteal, or perichondrial cells, with the latter being preferred. Further, such cells should be blastic, i.e. prepared to divide and produce repair tissue, as opposed to cells which are already differentiated such as cells from articular cartilage. Such autologous precursor cells for the production of connective tissue can be harvested from a variety of sources. Perichondrium, a thin tissue which is attached to the surface of cartilage, can be harvested from a portion of the ribs which is made of cartilage as diagramatically shown in FIG. 7. Chondrocytes can be harvested from cartilage, preferably articular cartilage, but also from cartilage of the ribs. They can also be harvested from growth plates from fetal tissue. Bone marrow is present in almost all of the bones of the body and can be harvested by inserting a needle into the space between the bone cortex where the marrow resides and by aspirating from that space. Periosteum is similar to perichondrium except that it invests all of the bones of the body and can be harvested by stripping off of the bone with instruments called periosteal elevators. The selection of the particular source of precursor cells centers around the availability of cells, i.e. the number of cells that can be harvested and the ease with which they can be harvested, as well as their ability to multiply in an in vitro environment and ultimately attach to a carrier for reimplantation. Perichondrium and periosteum have precursor cells which have to be freed from the surrounding tissue and their numbers are relatively small. Chondrocytes are cells that have already developed a phenotypic expression and have to be harvested from cartilage. Again, their numbers are relatively small compared to the amount of tissue that has to be harvested. Bone marrow is easily harvested but contains a mixture of various cells, and separation of the precursor cells has to be performed.

The precursor cells are then secured to the biodegradable device in a manner to maintain their viability and allow the cells to continue to grow, proliferate, and produce the repair matrix. As tissue, perichondrium and periosteum are cut to the desired size of the biodegradable device and can be attached to the biodegradable device by a suturing technique as diagramatically shown in FIG. 7, although other techniques such as gluing may be possible. The biodegradable device, attached tissue, and the chemotactic ground substance and preferably the biological modifiers are then transplanted to an articular cartilage defect which has been drilled to create a bone defect of equal surface dimension into which the biodegradable device is press fit to thereby secure the biodegradable device and the tissue sutured thereto in the bone defect which is diagramatically shown in FIG. 7. The precursor cells then proliferate and produce a matrix which is identical to normal articular cartilage while bone forms in the biodegradable device in contact with bone tissue, thereby repairing the bone and cartilage defect.

Being free cells, chondrocytes and bone marrow require in vitro technical capability and particularly are grown in culture, within or upon the biodegradable device, and need to attach to the biodegradable device by virtue of biological processes. Specifically, receptors in the cells' surface need to attach to the biodegradable device. In addition to enhancing the attractiveness of the biodegradable device for cellular attachment at the site of repair in order to effect that repair, the chemotactic ground substance which is an RGD attachment moiety of fibronectin in the most preferred form of the present invention facilitates the attachment of chondrocytes and bone marrow to the biodegradable device. Particularly, the precursor cells can be harvested from either perichondrium, periosteum or bone marrow. The precursor cells are cultured using standard cartilage culturing methods using either the techniques of 1) placing the precursor tissue in culture and allowing the cells to proliferate out of the tissue, or 2) digesting the tissue with collagenase, thereby freeing the cells, which in turn are placed in the culture medium and grown. When the precursor cells have grown to confluence (cells covering the surface of a culture plate), they are trypsinized to free them from their attachment to the culture plate and are suspended in culture medium at a high concentration in the range of 500 thousand-to-1.5 million per 1–5 milliliter solution. The dry biodegradable device is then placed in the culture medium, allowing the suspended cells to infiltrate the porous structure of the biodegradable device of the preferred form and become attached. By its hydrophilic nature, the biodegradable device in the preferred form formed of polylactic acid attracts the solution into it, thereby effecting transfer of the cells into the voids of the gross structure. This process of attachment may be assisted by the use of chemotactic and chemoattractant ground substances such as fibronectin and preferably an RGD attachment moiety of fibronectin. The biodegradable device may also be pretreated with growth factors, such as a transforming growth factor B or basic fibroblastic growth factor to assist the process of cell proliferation once the cells are attached to the biodegradable device. This composite of the biodegradable device and attached precursor cells is then implanted into the articular cartilage defect which has been drilled to create a bone defect of equal surface dimension into which the biodegradable device is press fit to thereby secure the biodegradable device and the cells cultured thereto in the bone defect as diagrammatically shown in FIG. 7.

It should be noted that the use of the biodegradable device to secure the periosteum graft or other source of precursor cells in the articular cartilage deficiency is particularly advantageous. Specifically, the press fit of the biodegradable device into the bone cavity locks the biodegradable device and the attached precursor cells into place without the use of a cover such as a periosteal cover which is very restrictive for use especially in humans. Also the biodegradable device including the periosteum graft or other source of precursor cells attached thereto has peripheral contact with the bone and/or cartilage inside of the lesion. Thus, the biodegradable device acts as an osteoconductive and chondroconductive agent serving as a template for bone and cartilage formation if it is in contact with bone and/or cartilage tissue.

It should also be noted that it is unnecessary to entrap the autologous cells in a matrix using the biodegradable device as a carrier. For example, collagen matrixes have been utilized by others but collagen can have a mild antigenicity and is structurally less strong than poly(hydroxy) acids.

In addition to being press fit into a drilled bone defect, the biodegradable device and attached precursor cells can be fabricated in a form to totally cover the surface of a joint, replicating the convexities or concavities as well as the dimensions of the joint—corresponding to the particular joint to be treated. In essence, the biodegradable device and attached precursor cells would cap the entire bone surface that contributes to the joint, achieving stability by virtue of an interference fit.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A biodegradable device for facilitating healing of voids in bone, cartilage as well as soft tissue comprising, in combination:

a. a porous macrostructure, made from a biodegradable polymer, providing a porous architecture as well as structural and mechanical integrity to the void being treated, with the porous macrostructure including interconnecting voids; and b. a porous microstructure, formed from a chemotactic ground substance and located in the voids and carried by and separate from the biodegradable polymer forming the porous macrostructure, with the chemotactic ground substance includes an RGD attachment moiety of fibronectin.

2. A biodegradable device for facilitating healing of structural voids in bone, cartilage as well as soft tissue comprising, in combination:

a. a porous macrostructure, made from a biodegradable polymer, providing a porous architecture as well as structural and mechanical integrity to the void being treated, with the porous macrostructure including interconnecting voids;

b. a porous microstructure, formed from a chemotactic ground substance and located in the voids and carried by and separate from the biodegradable polymer forming the porous macrostructure; and c. graft precursor cells carried by the porous macrostructure.

3. The device of claim 2 wherein the graft precursor cells are in the form of tissue sutured to the porous macrostructure.

4. The device of claim 2 wherein the graft precursor cells are in the form of free cells having receptors, with the free cells being attached to the porous macrostructure by permitting the receptors of the free cells to be engaged to the porous macrostructure.

5. The device of claim 4 wherein the chemotactic ground substance includes an RGD attachment moiety of fibronectin.

6. A biodegradable device for facilitating healing of structural voids in bone, cartilage as well as soft tissue comprising, in combination: a porous macrostructure, made from a biodegradable polymer, providing a porous architecture as well as structural and mechanical integrity to the void being treated, with the porous macrostructure including interconnecting voids; and graft precursor cells in the form of free cells having receptors, with the free cells being attached to the porous macrostructure by permitting the receptors of the free cells to be engaged to the porous macrostructure.

* * * * *

UNITED STATES PATENT AND TRADEMARK OFFICE
CERTIFICATE OF CORRECTION

PATENT NO. : 6,005,161
DATED : December 21, 1999
INVENTOR(S) : John H. Brekke

It is certified that error appears in the above-identified patent and that said Letters Patent is hereby corrected as shown below:

On the title page item [19], cancel "et al."

Item [75], cancel "Richard D. Coutts, San Diego, Calif."

Item [57], line 15 cancel "B" and substitute therefor -- $B$ --.

Column 2, line 60, cancel "B" and substitute therefor -- $B$ --.

Column 3, line 44, cancel "B" and substitute therefor -- $B$ --.

Column 10, line 39, cancel "B" and substitute therefor -- $B$ --.

Column 11, line 66, cancel "B" and substitute therefor -- $B$ --.

Column 12, line 48, before "voids", insert -- structural --.

Signed and Sealed this

Ninth Day of January, 2001

Attest:

Q. TODD DICKINSON

*Attesting Officer*  *Commissioner of Patents and Trademarks*